United States Patent [19]

Sanders

[11] Patent Number: 4,463,009
[45] Date of Patent: Jul. 31, 1984

[54] DIALKYL 1-(2-PYRIDINYLTHIO)-1,2-HYDRAZINEDICARBOXYLATE, N-OXIDES AND THEIR USE AS ANIMAL GROWTH STIMULANTS

[75] Inventor: Winfred J. Sanders, Mt. Holly, N.J.

[73] Assignee: SmithKline Beckman Corporation, Philadelphia, Pa.

[21] Appl. No.: 485,558

[22] Filed: Apr. 15, 1983

[51] Int. Cl.$^3$ .................... A61K 31/44; C07D 221/00
[52] U.S. Cl. .................................. 424/263; 546/293
[58] Field of Search ...................... 424/263; 546/293

[56] References Cited

U.S. PATENT DOCUMENTS 4,002,634  1/1977  Kalopissis et al. .................. 546/293

*Primary Examiner*—Sam Rosen
*Attorney, Agent, or Firm*—William H. Edgerton; Richard D. Foggio; Alan D. Lourie

[57] ABSTRACT

Dialkyl 1-(2-pyridinylthio)-1,2-hydrazinedicarboxylate, N-oxides are prepared by reacting a 2-mercaptopyridine-N-oxide and a dialkyl azodicarboxylate. The end products are useful as antimicrobial agents and, especially, growth promotants in monogastric meat producing animals. A species of the group is diethyl 1-(2-pyridinylthio)-1,2-hydrazinecarboxylate, N-oxide.

10 Claims, No Drawings

DIALKYL 1-(2-PYRIDINYLTHIO)-1,2-HYDRAZINEDICARBOXYLATE, N-OXIDES AND THEIR USE AS ANIMAL GROWTH STIMULANTS

This invention comprises new di-lower alkyl 1-(2-pyridinylthio)-1,2-hydrazinedicarboxylate, N-oxides and animal feed compositions containing them as active ingredients.

BACKGROUND OF THE INVENTION

Prior patent applications which are related to the present invention are U.S. Ser. No. 420,678, filed Sept. 21, 1982, covering "FEED COMPOSITIONS CONTAINING A (1-OXO-2-PYRIDYL)DISULFIDE" and U.S. Ser. No. 403,228, filed July 29, 1982 covering "FEED COMPOSITIONS CONTAINING COPPER SALTS OF 2-HYDROXYPYRIDINE-N-OXIDES". The new compounds and utilities of the present invention are believed to be distinct from the subject matter of those applications and from the publications cited therein.

DESCRIPTION OF THE INVENTION

The compounds of this invention are illustrated by the following structural formula:

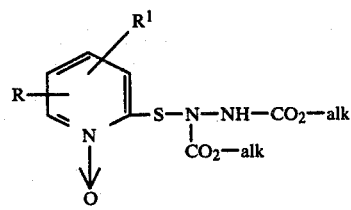

in which: R and $R^1$ are, each, hydrogen, $C_{1-6}$-alkyl, $C_{1-6}$-alkoxy, $C_{1-6}$-alkylthio, nitro, hydroxy, halo such as chloro or bromo, carboxy, phenyl, benzyl or benzylthio; and each alk is a lower alkyl of from 1-6 carbons.

A subgeneric group of this invention is represented by formula I in which R and $R^1$ are hydrogen. The prime species of this invention is the compound of formula 1 in which R and $R^1$ are hydrogen and alk is ethyl.

The compounds of this invention are prepared by reacting stoichiometric quantities of a known pyrithione (2-mercaptopyridine-1-oxide) and a known dialkylazadicarboxylate at about room temperature in an organic solvent such as ether, ethylene chloride or the like until reaction is substantially complete.

Examples of the compounds of this invention are diethyl 1-(2-pyridinylthio)-1,2-hydrazinedicarboxylate, N-oxide; dimethyl 1-(2-pyridinylthio)-1,2-hydrazinedicarboxylate, N-oxide; dimethyl 1-(3-methyl-2-pyridinylthio)-1,2-hydrazinedicarboxylate, N-oxide; diethyl 1-(6-methyl-2-pyridinylthio)-1,2-hydrazinedicarboxylate, N-oxide; diethyl 1-(3,5-dichloro-2-pyridinylthio)-1,2-hydrazinedicarboxylate, N-oxide; diethyl 1-(4-carboxy-2-pyridinylthio)-1,2-hydrazinedicarboxylate, N-oxide; dibutyl 1-(4,5-dimethoxy-2-pyridinylthio)-1,2-hydrazinecarboxylate, N-oxide; diethyl 1-(4-phenyl-2-pyridinylthio)-1,2-hydrazinedicarboxylate, N-oxide; diethyl 1-(5-benzyl-2-pyridinylthio)-1,2-hydrazinedicarboxylate, N-oxide or diethyl 1-(4,5-dibutoxy-2-pyridinylthio)-1,2-hydrazine dicarboxylate, N-oxide.

The feed compositions of this invention comprise the normal feed rations of the meat producing animals supplemented by a quantity of an active ingredient of formula I, which is effective for improving the growth rate and feed efficiency of the animals but which is not toxic or noxious to a degree that the animals will reduce ingestion of the ration. The quantity of the active ingredient will vary, as is known to the art, with factors such as the cost of the ingredient, the species and the size of animal, the relative activity of the compound of formula I or the type of feed ration used as the basal feed.

Representative feed rations for swine and poultry are in the examples presented hereafter. Swine feed from weanling to fattening or finishing rations may be supplemented. Swine eat from about 2 lb. of ration per day (for a 25 lb. pig) to 9 lb. per day (for a 150 lb. pig). Most rations are comprised of a corn base supplemented with legume silage, wheat bran, oats, barley, molasses or a protein supplement.

Poultry feeds comprise starter rations, broiler rations and laying rations. The rations are usually based on ground corn, corn meal or soybean meal. The broiler rations, often, contain high energy supplements such as added fats, proteins and vitamins. Turkey rations are similar, but comprise only a starting ration and a growing ration. Chickens or pheasants eat from 0.03–0.3 lbs. of feed per day, turkeys twice that much. Estimated intake of feed is dependent on the weight and age of the meat producing animal.

The active ingredients of formula I are mixed uniformly with such feed rations to give supplemented rations which are, then, fed as to custom, which is, most often, ad libitum. Conveniently, to do this, a premix of the supplemental growth promotant of this invention, optionally combined with or without other supplements known to this art such as an anthelmintic, a nitrogen source or an antibiotic, for example, virginiamycin or oxytetracycline is prepared by the manufacturer for sale to the formulators or feed lot operators. The concentration of S-hydrazopyrithiones in the premix is usually from 5–75% by weight or a concentration 100–2000 times greater than that in the complete feed ration. The premix form may be liquid or solid. Premix vehicles are corn oil, cottonseed oil, molasses or distillers solubles to form a liquid premix preparation. Sucrose, lactose, corn meal, ground corn, flour, calcium carbonate or soybean meal are often used as bases for solid premix preparations. The premix composition is, then, mixed uniformly with whole ration which is fed to the target animal. Such premix compositions are included in the term "feed compositions" as used herein.

The concentration of the 2-pyridinylthiohydrazinedicarboxylate, N-oxide of formula I in the complete ration is a nontoxic but active quantity chosen, for example, from a range of about 1–100 parts of active ingredient by weight per million parts of whole feed (ppm) or about 2–115 grams per ton. Advantageously, a nontoxic quantity of active ingredient is chosen from the range of 10–50 ppm of a compound of formula I.

The method of this invention comprises feeding to growing, monogastric, meat-producing animals, especially swine and poultry, an effective growth promoting but nontoxic quantity of a compound of formula I. Other monogastric animals whose digestive tract also features fermentation in a cecum or cecum-like chamber are rabbits and horses.

The supplemented feed rations, described above, are presented to the animal by methods known to the art. Ad libitum feeding in the pasture, pen or growing shed is most convenient to increase the growth rate of the animal and to increase the feed efficiency of the growing operation. Alternatively, the same supplemented feeds may be given to ruminant animals, particularly when the S-hydrazopyrithione of formula I is coated to bypass the upper stomach or rumen. Data presented in the in vitro working examples demonstrate that a selective effect as described hereinabove was not detected in the rumen.

The compounds of this invention have also been found to have chemotherapeutic activity such as: *C. albicans* (63 μg/ml); *Staph. aureus* (2.0 μg/ml); *Strep. faecalis* (3 μg/ml) and *E. coli* (63 μg/ml); m.i.c.'s for diethyl 1-(2-pyridinylthio)-1,2-hydrazinedicarboxylate, N-oxide.

The following working examples are intended to illustrate this invention. All percentages are by weight. All temperatures are Centigrade.

EXAMPLE 1

A swine ration for growing hogs of 40-100 pounds body weight is prepared using the following formula:

| | |
|---|---|
| Corn, ground | 78.15% |
| Soybean oil meal, 44% | 17.0% |
| Meat scraps, 50% | 3.0% |
| Oyster shell flavor | 0.4% |
| Bone meal | 0.5% |
| Zinc oxide | 0.01% |
| Vitamin A, B, $B_{12}$ & D supplement | optional |

The ration is supplemented to 100% with 40 ppm of diethyl 1-(2-pyridinylthio)-1,2-hydrazinedicarboxylate, N-oxide distributed through a premix carrier. The ration is fed, ad libitum, to the penned growing or fattening swine.

EXAMPLE 2

A chicken ration for broilers is prepared using the following formula:

| | |
|---|---|
| Yellow corn meal | 67.35% |
| Soybean oil meal | 24.00% |
| Menhaden fish meal | 6.00% |
| Steamed bone meal | 1.00% |
| Ground limestone | 1.00% |
| Iodized salt | 0.34% |
| 25% choline chloride | 0.13% |
| Vitamin $B_{12}$ | 0.10% |
| Manganese sulfate | 0.02% |
| Vitamin mix | 0.06% |

The ration is supplemented with 30 ppm of diethyl 1-(2-pyridinylthio)-1,2-hydrazinedicarboxylate, N-oxide and fed ad libitum to the chickens.

EXAMPLE 3

Chick Growth Study

A. Methodology:

One day old broiler chicks, selected for weight, health and sex, are housed in an environmentally controlled room with temperature at 80° F. and humidity at 40%. Chicks are fed ad libitum. Water is offered ad libitum. A rye or corn basal ration is fed during the acclimation period (days 1 and 2), then, mixed with the compound under test or control conditions on days 3-17. Either 8 pens (64 chicks) or 16 pens (128 chicks) are used for each test or control group.

| | Basal Rye Diet | |
|---|---|---|
| Diet Ingredients | (% w/w) | (lbs/ton) |
| Ground Rye (fine grind) | 54.4 | 1088 |
| Soybean Meal (49% protein) | 27 | 540 |
| Meat & Bone meal (50% protein) | 10 | 200 |
| Dehydrated Alfalfa meal | 1.25 | 25 |
| Fat, animal | 4 | 80 |
| Dried Whey (or lactose) | 1 | 20 |
| Ground Limestone | 0.67 | 13.4 |
| Dicalcium Phosphate | 0.50 | 10 |
| Iodized salt | 0.23 | 4.6 |
| Vitamin premix | 0.175 | * |
| Trace mineral premix | 0.25 | 5 |
| DL methionine (98%) | 0.45 | 9 |
| Choline Chloride (50% aqueous sol.) | 0.150** | 3 |

*Vitamin premix will be mixed into diets when test chemicals are added. 87.5 g vitamin premix/49,912.5 g of basal rye diet.
**Since choline is added as a 50% aqueous solution, percentage in diet is doubled.

B. Representative results using diethyl 1-(2-pyridinylthio)-1,2-hydrazinedicarboxylate, N-oxide:

| | Dose (ppm) | Reps (8/rep) | Weight | | Feed/Gain | | | Dead |
|---|---|---|---|---|---|---|---|---|
| | | | | | % of Control | | | |
| | | | 10 day | 17 day | 3-10 | 10-17 | 3-17 | |
| (1) | 20 | 8 | 96.4 | 103.2 | 102.2 | 101.7 | 101.7 | 1 |
| | 40 | 8 | 90.9 | 102.0 | 103.3 | 95.0 | 98.4 | 4 |
| Control | 0 | 8 | 164.0 g | 305.3 g | 1.541 g | 2.321 g | 1.956 g | 0 |
| (2) | 20 | 8 | 103.5 | 103.4 | 96.8 | 96.5 | 96.4 | 4 |
| (3) | 50 | 8 | 93.2 | 102.8 | 97.1 | 85.2 | 93.6 | 0 |

EXAMPLE 4

A. Methodology:

A Yorkshire barrow is surgically prepared either with an ileal cannula, which is placed 15 cm. from the ileo-ceco-colic junction, or a cecal cannula, which placed midway between the apex and origin of the cecum. The animal is fed 4 times daily to restrict intake to 4.5% of body weight in a 30 kg animal or 2.5% of body weight in a 100 kg animal. The swine grower ration is:

| | (% w/w) | (lbs/ton) |
|---|---|---|
| Medium ground shelled corn | 70.60 | 1412 |
| Soybean meal, 44% | 22.00 | 440 |
| Dehydrated alfalfa meal, 17% | 4.50 | 90 |
| Calcium propionate | 0.15 | 3 |
| Vitamin/mineral premix | 2.75 | 55 |

Sampling of the material, via the cannula, begins 150–180 minutes following the first morning feeding and continues any time from 30–120 minutes thereafter, depending on the quantity of material needed. The sample is maintained in crushed ice, no cooler than 5°, and is gassed continuously with carbon dioxide. The collected material is filtered. The filtrate is the inoculum used for incubations of the test and control samples. The gassed inoculum, 2.25 ml, is placed in each of 10 gassed test tubes, each containing 0.75 ml of a nutrient solution and 0.5 mg of each test compound. Four blank control tubes, along with the test compound tubes, are incubated 5 hours at 37° with agitation. Four more killed tubes are included which are not incubated.

The tubes are each treated with 0.60 ml of a 25% solution of metaphosphoric acid, then, stored at −4° until analysis. Samples are thawed and centrifuged for 25 minutes at 20,000 r.p.m. The supernatent liquid is decanted, sampled for gas chromatography and automatic analysis. The results are fed into a computer for finishing to give figures in which the blank control value is 100%. Virginiamycin is used as a positive control.

B. Representative results using diethyl 1-(2-pyridinyl-thio)-1,2-hydrazinedicarboxylate, N-oxide.

| | | VFA | LYS | GLU | LAC* |
|---|---|---|---|---|---|
| Diethyl 1-(2-pyridinylthio)-1,2-1,2-hydrazinedicarboxylate, N—oxide Ileal | | | | | |
| | | % of control values | | | |
| (1) | 166.7 ppm | 47 | 194 | 379 | 54 |
| | 16.67 ppm | 72 | 152 | 237 | 81 |
| | 1.67 ppm | 91 | 109 | 166 | 91 |
| (2) | 166.67 ppm | 55 | 110 | 845 | 139 |
| (3) | Control-virginiamycin | | | | |
| | 166.67 ppm | 86 | 144 | 496 | 14 |
| | 16.7 ppm | 114 | 141 | 464 | 12 |
| | 1.67 ppm | 255 | 99 | 393 | 0 |

*VFA refers to the total of volatile fatty acids, namely acetate, propionate, isobutyrate, butyrate, isovalerate and valerate. LYS is lysine, GLU is glucose and LAC is L-lactic acid.

EXAMPLE 5

Chemical Preparations

A mixture of 2.59 (0.0197 mmole) of 2-mercaptopyridine-N-oxide and 50 ml of anhydrous ether is stirred until the pyrithione dissolves. Diethyl azadicarboxylate (3.6 g, 0.0206 mmole, 95% pure) is added dropwise to the stirred reaction mixture at room temperature. After stirring for 1 hour, a white precipitate forms. Stirring is continued for another hour. The product is collected, washed and dried to give diethyl 1-(2-pyridinylthio)-1,2-hydrazinecarboxylate, N-oxide, m.p. 137°–139°.

Anal. Calcd. for $C_{11}H_{15}N_3O_5S$: C, 43.85; H, 5.02; N, 13.19. Found: C, 44.13; H, 4.88; N, 13.68.

Other representative compounds of this invention are prepared in the same manner by reacting one equivalent of the known pyrithione with a slight excess of the known azadicarboxylate ester.

| Pyrithione | Azodicarboxate | Product |
|---|---|---|
| 4-methyl | diethyl | diethyl 1-(4-methyl-2-pyridinyl-thio)-1,2-hydrazinedicarboxylate, N—oxide |
| 3-methyl | dimethyl | dimethyl 1-(3-methyl-2-pyridinyl-thio)-1,2-hydrazinedicarboxylate, |

-continued

| Pyrithione | Azodicarboxate | Product |
|---|---|---|
| | | N—oxide |
| 6-methyl | dibutyl | dibutyl 1-(6-methyl-2-pyridinyl-thio)-1,2-hydrazinedicarboxylate, N—oxide |
| 3,5-dichloro | diethyl | diethyl 1-(3,5-dichloro-2-pyridinylthio)-1,2-hydrazinedicarboxylate, N—oxide |
| 4-carboxy | diethyl | diethyl 1-(4-carboxy-2-pyridinyl-thio)-1,2-hydrazinedicarboxylate, N—oxide |
| 4-benzyl | diethyl | diethyl 1-(4-benzyl-2-pyridyl-thio)-1,2-hydrazinedicarboxylate, N—oxide |
| 4,5-dimethoxy | diethyl | diethyl 1-(4,5-dimethoxy-2-pyridinylthio)-1,2-hydrazinedicarboxylate, N—oxide |
| 4-phenyl | diethyl | diethyl 1-(4-phenyl-2-pyridinyl-thio)-1,2-hydrazinedicarboxylate, N—oxide |
| 5-benzyl | dimethyl | dimethyl 1-(5-benzyl-2-pyridinyl-thio)-1,2-hydrazinedicarboxylate, N—oxide |
| 4,5-dibutoxy | diethyl | diethyl 1-(4,5-dibutoxy-2-pyridinylthio)-1,2-hydrazinedicarboxylate, N—oxide |

What is claimed is:

1. A chemical compound of the formula:

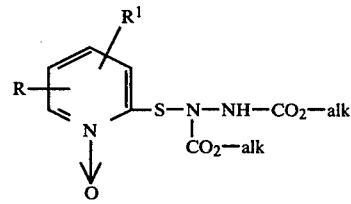

in which:

R and $R^1$ are, each, hydrogen, $C_{1-6}$-alkyl, $C_{1-6}$-alkoxy, $C_{1-6}$-alkylthio, nitro, hydroxy, halo, carboxy, phenyl, benzyl or benzylthio, and alk is lower alkyl of 1–6 carbons.

2. The compound of claim 1 being diethyl 1-(2-pyridinylthio)-1,2-hydrazinedicarboxylate, N-oxide.

3. The compound of claim 1 in which each alk is ethyl.

4. The compound of claim 1 in which R and $R^1$ are hydrogen.

5. An animal feed composition supplemented by a nontoxic quantity of a compound of claim 1 which is effective for increasing the growth rate and feed efficiency of a meat producing, monogastric animal.

6. The animal feed composition supplemented by a nontoxic quantity of a compound of claim 2 which is effective for increasing the growth rate and feed efficiency of a meat producing, monogastric animal.

7. The composition of claim 5 in which the form of said composition is a whole animal feed containing a nontoxic quantity of compound selected from the range of 5–50 ppm.

8. The composition of claim 5 in which the composition is a premix feed composition.

9. A method of improving the weight gain and feed efficiency of meat producing, monogastric animals comprising feeding said animals an effective therefor but nontoxic quantity of a compound of claim 1.

10. The method of improving the weight gain and feed efficiency of meat producing, monogastric animals comprising feed said animals an effective therefor but nontoxic quantity of a compound of claim 2.

* * * * *